United States Patent
Partelow (12)

(10) Patent No.: US 6,300,324 B1
(45) Date of Patent: Oct. 9, 2001

(54) COMPOSITION FOR REPELLING TICKS

(76) Inventor: Scott E. Partelow, P.O. Box 2235, Sag Harbor, NY (US) 11963

( * ) Notice: Subject to any disclaimer, the term of this patent is extended or adjusted under 35 U.S.C. 154(b) by 0 days.

(21) Appl. No.: 09/224,794

(22) Filed: Jan. 4, 1999

(51) Int. Cl.$^7$ .......................... A01N 57/26; A01N 25/00; A01N 33/18; A01N 43/00; A01N 65/00
(52) U.S. Cl. .................. 514/78; 424/195.1; 424/405; 424/DIG. 10; 514/52; 514/276; 514/277; 514/345; 514/474; 514/728; 514/918; 514/919
(58) Field of Search ..................... 424/405, 450, 424/195.1, DIG. 10; 514/52, 276, 474, 739, 728, 277, 345, 78, 918, 919

(56) References Cited

U.S. PATENT DOCUMENTS

| | | | |
|---|---|---|---|
| 4,759,930 | * | 7/1988 | Granierer et al. ............... 424/659 |
| 5,246,693 | * | 9/1993 | Grollier et al. ............... 424/450 |
| 5,362,425 | * | 11/1994 | Schrier ............... 264/4.6 |
| 5,466,458 | * | 11/1995 | Wilson ............... 424/407 |
| 5,518,736 | * | 5/1996 | Magdassi et al. ............... 424/451 |
| 5,589,181 | * | 12/1996 | Bencsits ............... 424/405 |
| 5,594,029 | * | 1/1997 | Bencsits ............... 514/552 |
| 5,635,174 | * | 6/1997 | Warren et al. ............... 424/84 |

FOREIGN PATENT DOCUMENTS 198 00 982-A1 * 7/1999 (DE).

OTHER PUBLICATIONS

U.S. Trademark Electronic Search System (TESS) (http://tess.uspto.gov), PhytoShield®, p. 1.*
Phytoshield®, Skin Care Essentials (http://www.abratherapeutics.com/ingredients/essentials.html), pp. 1,2.*

* cited by examiner

Primary Examiner—Jose' G. Dees
Assistant Examiner—Frank Choi
(74) Attorney, Agent, or Firm—Michael I. Kroll

(57) ABSTRACT

A composition (10) for repelling ticks and other insects contains a combination of plant extracts (14) in a topical liquid carrier (12). The plant extracts (14) include lavender (26), rosemary (30), thyme (32), aloe vera (28) and eucalyptus (34). The composition can further include one or more vitamins (18) such as Vitamin $B_1$ (36), Vitamin $B_6$ (38), Vitamin $B_{12}$ (40) and Vitamin C (42). Lecithin (16) may be included as an additional insect repelling component and also to assist dispersion of the various active components in the liquid carrier (12).

4 Claims, 2 Drawing Sheets

Carrier Liquids

12
- 20 Water
- 22 Oil
- 24 Alcohol

Plant Extracts

14
- 26 Lavender
- 28 Aloe vera
- 30 Rosemary
- 32 Thyme
- 34 Eucalyptus

Vitamins

13
- 36 $B_1$ (Thiamin)
- 38 $B_6$ (pyridoxine, pyridoxamine and pyridoxal)
- 40 $B_{12}$ (cyanocobalamin)
- 42 C (Ascorbic Acid)

Fig. 2

COMPOSITION FOR REPELLING TICKS

BACKGROUND OF THE INVENTION

1. Field of the Invention

Most commercial insect repellents contain, as the primary active component, the chemical diethytoluamide (DEET). Recently, however, many concerns have been raised regarding the topical administration of compositions containing DEET, particularly among children. These concerns have resulted in the Environmental Protection Agency (EPA) announcing that it is now banning manufacturers from claiming any DEET-containing composition to be "safe for kids." Even when used properly by adults, DEET has been known to cause rashes, seizures and irritability. Accordingly, DEET-free insect repellents are finding favor with consumers.

The instant invention relates generally to topically applied compositions for repelling insects and more specifically to compositions made from natural products for repelling ticks.

2. Description of the Related Art

Compositions for repelling or killing insects are known in the art. For example, U.S. Pat. No. 4,759,930 (Granirer, M. S. et al., Jul. 26, 1988) discloses an insecticidal composition which contains pyrethrum, rotenone, or both, and one or more of the following: eucalyptus, rosemary, peppermint and boric acid.

U.S. Pat. No. 5,466,459 (Wilson, W. R., Nov. 14, 1995) discloses an insecticidal composition having capsaicin as its active ingredient, in a refined wax base.

U.S. Pat. No. 5,589,181 (Bencsits, F., Dec. 31, 1996) discloses an insect repelling composition containing at least one fatty acid alkyl ester and at least one fatty alcohol in a fatty oil carrier.

U.S. Pat. No. 5,594,029 (Bencsits, F., Jan. 14, 1997) discloses the use of a coconut fatty acid as an insect repelling agent.

U.S. Pat. No. 5,635,174 (Warren, C. B., et al., Jun. 3, 1997) discloses an insect repelling composition containing geraniol in combination with citronellol and/or nerol. This patent further discloses the use of lavender absolute in an insect-attracting composition.

SUMMARY OF THE INVENTION

The present invention is concerned with a topically applied composition for repelling insects and more specifically to compositions made from natural products for repelling ticks.

A primary object of the present invention is to provide an insect and tick repelling composition which is free of DEET and other irritating, synthetic chemicals.

Another object of the present invention is to provide an insect and tick repelling composition which contains, as the active components therein, a combination of natural and naturally-derived substances.

An additional object of the present invention is to provide an insect and tick repelling composition which contains, as the active components therein, a combination of plant-derived materials.

Another object of the present invention is to provide an insect and tick repelling composition which contains, as the active components therein, one or more plant-derived materials selected from lavender, aloe vera, rosemary, thyme, eucalyptus, agrimony, wormwood, mugwort, pennyroyal, sweet woodruff, tansy, geraniol and marigold.

A further object of the present invention is to provide an insect and tick repelling composition which contains lecithin.

Another object of the present invention is to provide an insect and tick repelling composition which contains one or more vitamins selected from Vitamin $B_1$, Vitamin $B_6$, Vitamin $B_{12}$ and Vitamin C.

Another object of the present invention is to provide an insect and tick repelling composition which is non-irritating and safe for adults, children and animals when topically applied to the skin, fur or clothing.

Another object of the present invention is to provide an insect and tick repelling composition which is easy to use and economical to manufacture.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views.

FIG. 2 is a chart illustrating specifically the various components which may find use in the present invention.

DESCRIPTION OF THE PREFERRED EMBODIMENTS

Figure 1:
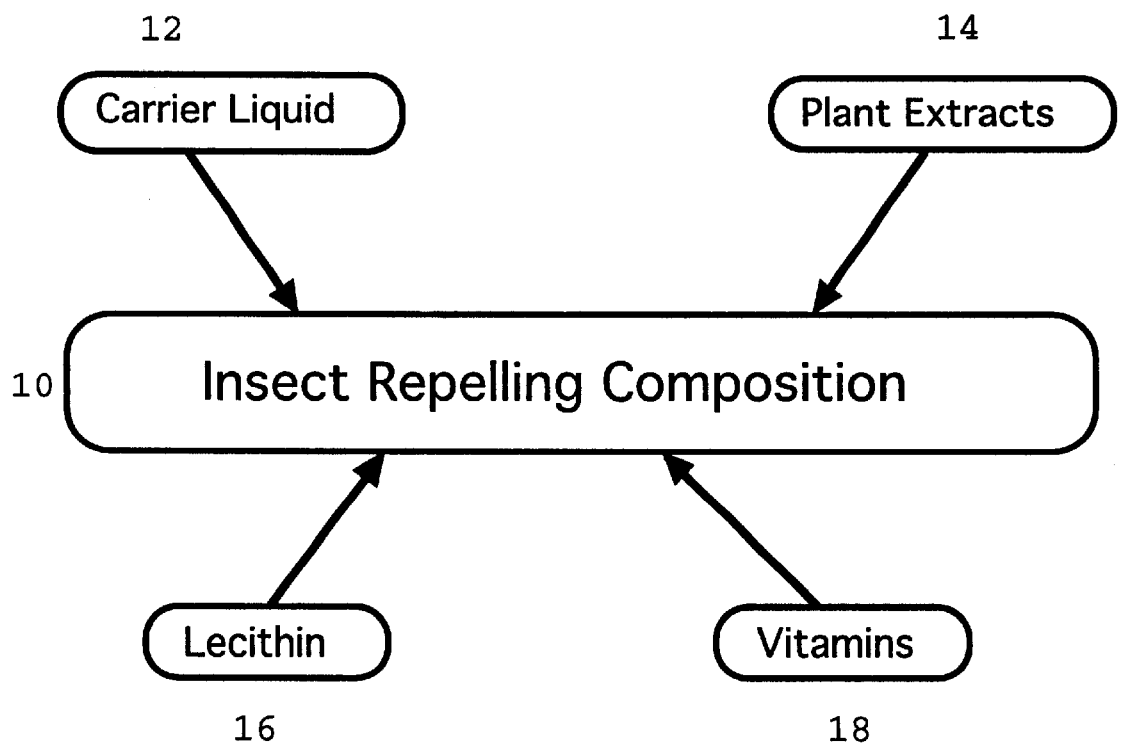
FIG. 1 is a diagrammatic view illustrating generally the various components which may find use in the present invention.

Turning now descriptively to the drawings, in which similar reference characters denote similar elements throughout the several views, the Figures illustrate an insect repellent of the present invention. With regard to the reference numerals used, the following numbering is used throughout the various drawing figures.

10 insect and tick repelling composition of the present invention
12 carrier liquid for 10
14 plant extract component of 10
16 lecithin component of 10
18 vitamin component of 10
20 water, the preferred carrier liquid for 10
22 oil
24 alcohol
26 lavender
28 aloe vera
30 rosemary
32 thyme
34 eucalyptus 36 Vitamin $B_1$
38 Vitamin $B_6$
40 Vitamin $B_{12}$
42 Vitamin C FIGS. 1 and 2 illustrate a tick and other insect repelling composition 10 which contains a combination of plant extracts 14 in a topical liquid carrier 12. The preferred plant extracts 14 include, for example, lavender 26, rosemary 30, thyme 32, aloe vera 28 and eucalyptus 34. In its preferred embodiment, the present invention further includes one or more vitamins 18, for example, Vitamin $B_1$ 36, Vitamin $B_6$ 38, Vitamin $B_{12}$ 40 and Vitamin C 42. Lecithin 16 may be included as an additional insect repelling component and also to facilitate dispersion of the various active components of the invention in the liquid carrier 12.

The carrier liquid 12 can be any suitable liquid which is non-toxic when applied topically. Examples include water 20, the preferred carrier, oils 22, alcohols 24 and combinations of the foregoing. Suitable oils include, for example, vegetable oils such as almond oil, macadamia nut oil, jojoba oil (which is technically a wax which remains liquid at room temperature) and the like, and mineral oils. Examples of suitable alcohols include isopropyl (rubbing) alcohol, ethyl alcohol and the like.

The active (insect-repelling) components of the compositions of the present invention are generally plants and plant-derived materials 14, in addition to lecithin 16. Speaking generally, any suitable form of the plant may be used, for example, raw plant material, essential oils of the plants which are prepared by conventional methods such as steam distillation and $CO_2$ extractions, and solvent-produced derivatives such as concretes and absolutes. While all forms are within the scope of the invention, the preferred forms are raw plant material and essential oils.

With regard to the choice of plant material 14, many plants may be suitably employed, including those known to possess insect-repelling characteristics and those not so known. Examples of plants which may be employed in the present invention include lavender 26, aloe vera 28, rosemary 30, thyme 32, eucalyptus 34, agrimony, wormwood, mugwort, pennyroyal, sweet woodruff, tansy, geranium and marigold. The preferred plants are lavender 26, aloe vera 28, rosemary 30, thyme 32 and eucalyptus 34.

A preferred active component of the invention is lecithin 16, the generic name for a class of plant and animal-derived monoaminomonophospholipids. Lecithins are the esters of oleic, stearic, palmitic, or other fatty acids with glycerolphosphoric acid and choline. The most common form of lecithin is 3-sn-phosphatidylcholine. In addition to providing insect-repelling characteristics to the composition, lecithin also acts as an emulsifier, which assists in dispersing any immiscible components such as the aforementioned essential oils, in water.

In addition to the aforementioned active ingredients, the composition of the present invention can also contain other, optional ingredients. A preferred class of these additional ingredients are nutritional vitamins 18 for promoting healthy skin (or fur/hide for animal use).

As with the plant material 14, a wide variety of vitamins 18 may be employed in the present invention. The preferred vitamins are Vitamin $B_1$ 36, Vitamin $B_6$ 38, Vitamin $B_{12}$ 40 and Vitamin C 42.

Vitamin $B_1$ 36 is known also as thiamin. The hydrochloride and nitrate salts of thiamin and thiamin alkyl disulfides such as the prophyidisulfide, tetrahydrofurfuryl disulfide, O-benzoyl disulfide can all be used in the present invention.

Vitamin $B_6$ 38 is the generic name for pyridoxine, its amine (pyridoxamine) and its aldehyde (pyridoxal). Vitamin $B_6$ can be selected from hydrochloride salts or 5'-phosphates of pyridoxine, pyridoxamine or pyridoxal. The preferred Vitamin $B_6$ is pyridoxine hydrochloride.

Vitamin $B_{12}$ 40 is also known as cyanocobalamin. Sources of Vitamin $B_{12}$ are, for example, cyanocobalamin, methylcobalamin, adenosylcobalamin, hydroxocobalamin and the like. Cyanocobalamin is preferred.

The most common, and preferred, form of Vitamin C 42 is l-ascorbic acid. However, other forms of Vitamin C, for example, d-ascorbic acid, dl-ascorbic acid, d-araboascorbic acid, dehydroascorbic acid and esters of ascorbic acid may also be used.

In accordance with the present invention, there is provided a composition for repelling ticks comprising the following in a topically applicable liquid carrier of water:

lavender flowers about 20 to about 35 weight percent;

lecithin about 20 to about 35 weight percent;

aloe vera about 15 to about 30 weight percent;

rosemary about 5 to about 15 weight percent;

thyme about 5 to about 15 weight percent;

eucalyptus oil about 1 to about 10 weight percent;

Vitamin B1 about 0.1 to about 1 weight percent;

Vitamin B6 about 0.1 to about 1 weight percent;

Vitamin B12 about 0.1 to about 1 weight percent; and

Vitamin C about 0.1 to about 1 weight percent.

The preceding composition would in one preferred embodiment have the above ingredients in the following proportions:

lavender flowers about 29 weight percent;

lecithin about 29 weight percent;

aloe vera about 19 weight percent;

rosemary about 10 weight percent;

thyme about 10 weight percent;

eucalyptus oil about 3 weight percent;

Vitamin B1 about 0.3 weight percent;

Vitamin B6 about 0.3 weight percent;

Vitamin B12 about 0.3 weight percent; and

Vitamin C about 0.3 weight percent.

EXAMPLES

The following examples of compositions of the present invention were prepared according to conventional methods known in the art.

Example 1

An aqueous composition of the present invention was prepared by adding the following ingredients to 5 gallons (19 l) of water.

| | |
|---|---|
| Lavender flowers | 6 oz. (170 g, 28.6 weight percent) |
| Lecithin | 6 oz. (170 g, 28.6 weight percent) |
| Aloe vera | 4 oz. (113 g, 19.0 weight percent) |
| Rosemary | 2 oz. (57 g, 9.6 weight percent) |
| Thyme | 2 oz. (57 g, 9.6 weight percent) |
| Eucalyptus oil | 20 ml (~19 g, 3.4 weight percent) |
| Vitamin $B_1$ | 2 g (0.3 weight percent) |
| Vitamin $B_6$ | 2 g (0.3 weight percent) |
| Vitamin $B_{12}$ | 2 g (0.3 weight percent) |
| Vitamin C | 2 g (0.3 weight percent) |

After maceration, the solids were strained out of the liquid, leaving the aqueous insect repelling composition of the invention.

Example 2

In a manner similar to that described in Example 1, above, a composition was made comprising water, lecithin, rosemary, agrimony, marigold, lavender, Vitamin $B_1$, and Vitamin $B_6$.

Example 3

In a manner similar to that described in Example 1, above, a composition was made comprising water, lecithin, eucalyptus, lavender, Vitamin $B_1$, Vitamin $B_6$ and Vitamin C.

Example 4

To five gallons of water, the following were added
2 cups alfalfa, cut and sifted
2 cups peppermint, cut and sifted
2 cups lemon grass, cut and sifted
2 cups rosemary, whole leaf
1 cup lecithin, granular
1 tablespoon vitamin C, powdered The mixture was heated to just below boiling (about 95° C.) and allowed to steep for about two hours in order to extract the plant material. The mixture was strained to remove the solid material, and 2 cups of geraniol were added and mixed thoroughly into the composition.

Example 5

A tick repelling composition was prepared as described in Example 4, except that peppermint oil was used in place of peppermint plant material and lemon grass oil was used in place of lemon grass plant material. Both oils were added to the composition at the same time as the geraniol.

Example 6

To five gallons (19 liters) of water, the following were added.
4 ounces (118 ml) peppermint oil
4 ounces (118 ml) lemon grass oil
4 ounces (118 ml) rosemary oil
16 ounces (472 ml) liquid lecithin The oils and the liquid lecithin were added to the water and mixed well to disperse the oils.

The compositions were tested for their ability to repel ticks (*Ixodes dammini*). All were shown to have high efficacy in repelling ticks.

It will be understood that each of the elements described above, or two or more together, may also find a useful application in other types of applications differing from the type described above. While the invention has been illustrated and described as embodied in a composition for repelling ticks and other insects, it is not intended to be limited to the details shown, since it will be understood that various omissions, modifications, substitutions and changes in the forms and details of the formulation illustrated and in its operation can be made by those skilled in the art without departing in any way from the spirit and scope of the present invention. For example, any suitable insect repelling plant material may be used instead of the specific plants described. Also, the carrier liquid may be any non-toxic liquid appropriate for topical use, in addition to the water, oils and alcohols described. And although ticks have been described, it should be appreciated that the composition herein described is also suitable for repelling a wide variety of pest insects such as chiggers, mosquitoes, flies, or any other undesirable pest such as spiders. Additionally, although the vitamin component of the present invention has been described herein as a skin/fur/hide conditioning component, it should be borne in mind that this component possibly provides insect repelling activity also, in addition to the lecithin and plant material. It should also be readily appreciated that the compositions of the present invention can be used on humans and any other animal which is desired to be protected from such pests. Furthermore, a wide variety of skin conditioning/treating components such as moisturizers and nutrients may be used instead of or in addition to the vitamins described.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed is:

1. A method of preparing a composition for repelling ticks comprising the steps of:

a) adding the following ingredients to water:
lavender flowers about 20 to about 35 weight percent;
lecithin about 20 to about 35 weight percent;
aloe vera about 15 to about 30 weight percent;
rosemary about 5 to about 15 weight percent;
thyme about 5 to about 15 weight percent;
eucalyptus oil about 1 to about 10 weight percent;
Vitamin B1 about 0.1 to about 1 weight percent;
Vitamin B6 about 0.1 to about 1 weight percent;
Vitamin B12 about 0.1 to about 1 weight percent; and
Vitamin C about 0.1 to about 1 weight percent; and b) after maceration, straining solids out of the liquid, leaving an aqueous tick repelling composition.

2. A composition produced by the method of claim 1.

3. A method of preparing a composition for repelling ticks comprising the steps of:

a) adding the following ingredients to water:
lavender flowers about 29 weight percent;
lecithin about 29 weight percent;
aloe vera about 19 weight percent;
rosemary about 10 weight percent;
thyme about 10 weight percent;
eucalyptus oil about 3 weight percent;
Vitamin B1 about 0.3 weight percent;
Vitamin B6 about 0.3 weight percent;
Vitamin B12 about 0.3 weight percent; and
Vitamin C about 0.3 weight percent; and b) after maceration, straining solids out of the liquid, leaving an aqueous tick repelling composition.

4. A composition produced by the method of claim 3.

* * * * *